Figure 1:
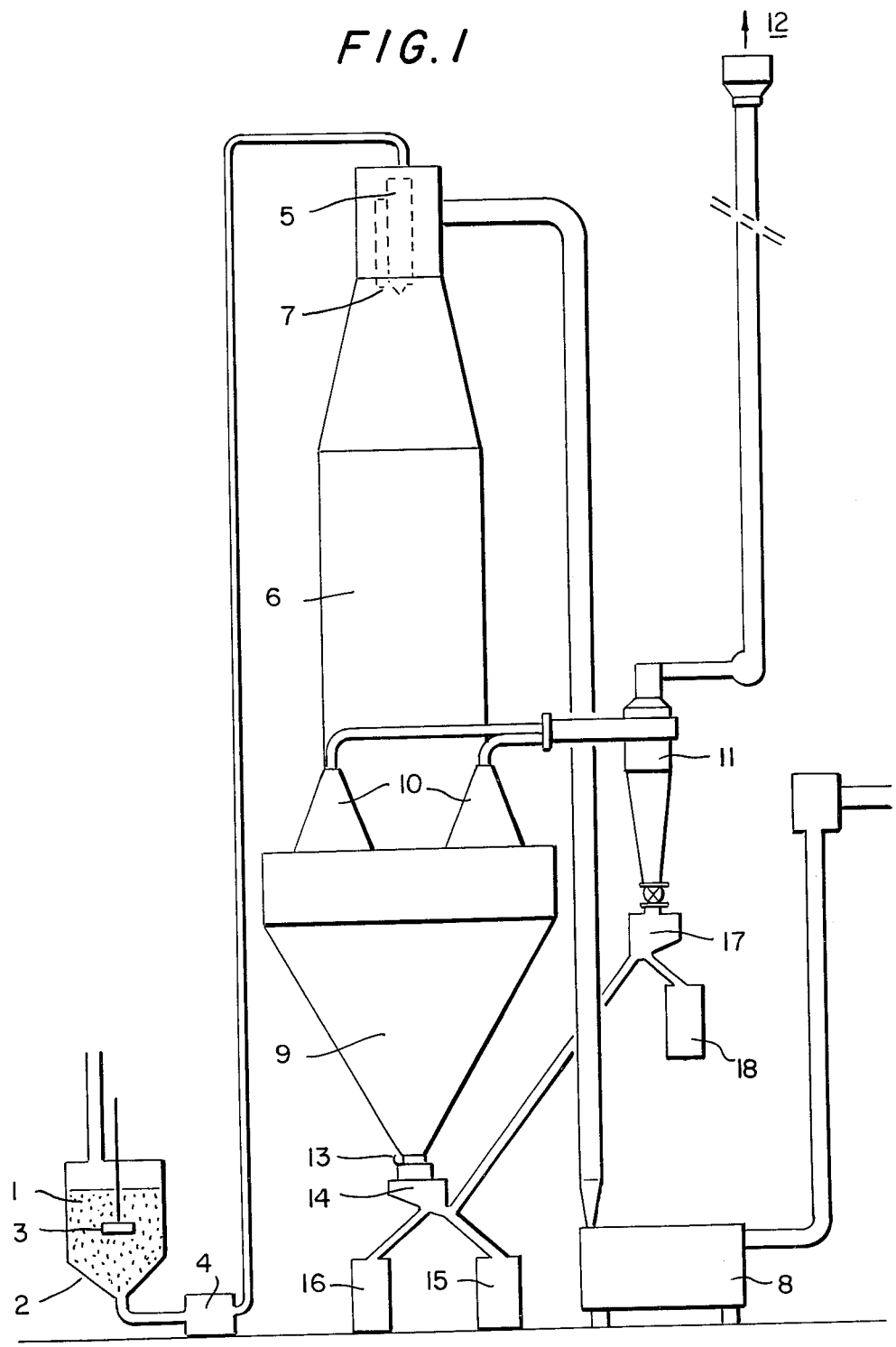

United States Patent [19]

Seager

[11] 4,016,254
[45] Apr. 5, 1977

[54] PHARMACEUTICAL FORMULATIONS

[75] Inventor: Harry Seager, Worthing, England

[73] Assignee: Beecham Group Limited, Great Britain

[22] Filed: Apr. 5, 1976

[21] Appl. No.: 673,441

Related U.S. Application Data

[63] Continuation of Ser. No. 360,828, May 16, 1973, abandoned.

[30] Foreign Application Priority Data

May 19, 1972 United Kingdom ............ 23576/72

[52] U.S. Cl. ................................ 424/33; 252/316; 424/80; 424/271
[51] Int. Cl.² ................ A61K 9/50; A61K 31/43; A61K 31/79
[58] Field of Search ............................ 424/19–22, 424/32–33, 78–83; 252/316

[56] References Cited

UNITED STATES PATENTS

| 3,634,586 | 1/1972 | Kaser et al. | 424/80 |
| 3,639,306 | 1/1972 | Sternberg et al. | 252/316 |
| 3,725,556 | 4/1973 | Hanssen et al. | 424/357 |

FOREIGN PATENTS OR APPLICATIONS 1,287,431  8/1972  United Kingdom

Primary Examiner—Shep K. Rose

[57] ABSTRACT

Microcapsules which have an average diameter of from $100\mu$ to $300\mu$ and which comprise 94% to 99.9% of a medicament coated by 0.1% to 6% of a coating agent may be formed into a powder with 0% to 95% excipients or a tablet or capsule with a carrier.

48 Claims, 3 Drawing Figures

VARIATION OF PARTICLE SIZE WITH COATING AGENT

VARIATION OF QUANTITY OF MICROCAPSULES OF DIAMETER < 75μ PRODUCED (PRIOR TO SEPARATION) WITH COATING AGENT CONCENTRATION

PHARMACEUTICAL FORMULATIONS

CROSS REFERENCE

This is a continuation, of Ser. No. 360,828, filed May 16, 1973; now abandoned.

The present invention relates to pharmaceutical compositions. More specifically, this invention relates to powders comprising microencapsulated medicament, to a process for the manufacture of such powders, to pharmaceutical compositions prepared from such powders and to methods of preparing such pharmaceutical compositions.

When used herein with respect to the novel powders of the invention, the term "powder" means a dustless, free-flowing powder.

When used herein the term "dustless " when applied to a powder means that the powder is substantially free from microcapsules of diameter less than $50\mu$. Normally and preferably, dustless powders contain no microcapsules of diameter less than $50\mu$. Under ideal conditions such dustless powders contain no microcapsules of diameter less than $75\mu$ but a powder will for almost all practical purposes be considered to be dustless if it contains less than 2% of microcapsules of diameter less than $75\mu$.

When used herein the term "free-flowing" when applied to a powder means that the powder has an angle of repose less than 40°.

When used herein the term "microcapsule" means a particle composed of an outer generally porous shell of coating agent with an inner core of fine particles. The core may contain small quantities of air and interspersed strands of coating agent. The shell material may be continuous or may contain depressions or "blow holes" giving access to the core from the outside. Thus a powder comprising "microencapsulated medicament" will contain microcapsules comprising medicament with a shell of coating agent.

When used herein to term "medicament" means an organic therapeutically useful substance.

When used herein the term "conventional pharmaceutical excipients" means excipients used in pharmaceutical formulations to improve the quality of the formulation or to increase the ease of preparation of the formulation and includes binders, lubricants, flavours, colours, disintegrants and the like. When calculating the percentage of such excipients present, the coating agent present in the medicament containing microcapsules is not included.

When used herein the term "coating agent" means one or more synthetic or naturally occuring polymers, gums or resins which are pharmaceutically acceptable.

When used herein percentages are calculated on a weight/weight basis unless otherwise stated.

The processing of medicaments from the initial production of the compound to the formulated product ready for use normally involves a milling stage. Milling is included to reduce the particle size of the medicament, to improve the drying rate of the material, to aid in blending operations, to increase the bioavailability of the medicament from the formulation or for various other reasons. Unfortunately, if the milling operation is sufficient to reduce the average medicament particle size to the desired range, then a small but significant proportion of the medicament becomes sufficiently finely divided to form a disadvantageous dust. Unless extensive and inconvient special handling techniques are used, generally some of the dust gets released into the atmosphere where it constitutes a health hazard and can lead to cross-contamination of active materials. The health hazard from airborne particles is particularly high when people can become sensitized to the medicament, for example, as with penicillins. Attempts to reduce the dust hazard by replacing the initial dry milling stage by a wet milling operation are not normally successful at this merely delays the formation of the dust to a subsequent drying or handling stage.

There has now been invented a spray drying process which, if used as part of the normal production of the medicament, eleviates or removes problems concerned with atmospheric dust. Further, the products of this process (whether the process is operated on the unfinished medicament taken from the production line or on an already conventionally completed product), are powders which are generally easily processed into standard dosage forms than the corresponding non-microencapsulated medicament and may also have other advantages such as increased stability with a corresponding increase in useful shelf-life, improved bulk densities, improved flowabilities and other beneficial properties.

These powders are novel and therefore form an important aspect of this invention.

Accordingly, the present invention provides a powder comprising 0% to 95% of conventional pharmaceutical excipients and 5% to 100% of microcapsules which microcapsules have an average diameter of from $100\mu$ to $300\mu$ and which comprise 94% to 99.9% of a medicament coated by 0.1% to 6% of a coating agent.

The limits for the average diameter of the microcapsules are set at $100\mu$ and $300\mu$ because if the average diameter falls below this range the powder is likely to be dusty and if the average diameter is above this range the biovalability of the medicament may be reduced.

The lower limit of 0.1% for the quantity of coating agent in the microcapsules is chosen because if smaller quantities of coating agent are used the microcapsules tend to be of poor quality. The upper limit of 6% is chosen in order to keep the costs of the process low and to ensure acceptable biopharmaceutical properties.

Any conventional pharmaceutical excipient present may also if desired, be microencapsulated with a coating agent. If any excipients present are microencapsulted they are generally but not necessarily coated by the same coating agent which is used in the medicament containing microcapsules.

The quantity of conventional pharmaceutical excipients present depends inter alia on the potency of the medicament. For example, a highly potent medicament required in doses of only a few milligrams may be diluted with large quantities of excipients, a medium potency medicament required in doses of a few tens of milligrams may be diluted with once or twice its weight of excipients whereas a low potency medicament which may be required in doses of one or more hundred milligrams may be used with only small quantities of excipients.

Generally, if some diluent effect is required the excipients may form from 5% to 95% of the powder.

However, in order to retain the greatest versitility for the powder (that is to enable it to be used in preparing the greatest number of different kinds of formulations for example, capsules, tablets, syrups, or the like), the quantity of conventional pharmaceutical excipient present, added during or after preparation is preferably below 5%. It is believed that the most versatile powders contain less than 2% of such excipients, preferably less than 1%, for example, 0% or approximately 0%.

Thus, one favoured form of this aspect of the invention provides a powder containing at least 95% of microencapsulated medicament and preferably approximately 100% of microencapsulated medicament.

As previously stated, it is generally considered preferable to keep the quantity of synthetic formulation aids as low as possible. For this reason, and for reasons of economy, it is usually preferred to keep the quantity of coating agent as low as compatible with good microcapsule quality. With cost coating agents, microcapsules of high quality are more easily prepared if there is two or more times the minimum quantity of coating agent present (that is, at least 0.2%).

The interplay of the preceding factors result in a particularly suitable range of quantities of coating agent in the microcapsules being 0.1% to 2.5%, preferably 0.2% to 2% and most preferably about 0.2% to 1.5%.

In order to ensure the dustless properties of the powder of the invention and at the same time retain the bioavailability of the medicament, at least 90% of the microcapsules should have diameters in the range $75\mu$ to $45\mu$, more suitably 95% of the microcapsules should have a diameter in this size range and preferably 99% of the microcapsules should have diameters in this size range.

It is believed that suitable powders are comprised of microcapsules at least 80% of which have diameters between $100\mu$ and $300\mu$. In general, microcapsules with such characteristics will have an average diameter of at least $150\mu$ but less than $250\mu$, for example, from approximately $150\mu$ to $225\mu$.

In practice, it has been found that certain favourable powders of the present invention comprise 98% to 100% of microcapsules which microcapsules have diameter of at least $100\mu$, 90% of which microcapsules have diameters in the range $75\mu$ to $450\mu$ and which microcapsules comprise 0.1% to 2.5% of coating agent and 97.5% and 99.9% of medicament.

For the greatest versatility, such powders consist essentially of microcapsulated medicament. Generally, these powders may consist essentially of microcapsules containing 0.2% to 2.0% coating agent and often the microcapsules in such powders may contain less than 1% of coating agent.

Generally, powders having particularly good bioavailability and versitility consist essentially of microcapsules comprising 98% to 99.9% medicament and 0.2% to 2% coating agent which microcapsules have an average diameter between $150\mu$ to $250\mu$, 95% having diameters between $75\mu$ to $450\mu$ and 80% of which have diameters between $100\mu$ to $300\mu$. Frequently, the microcapsules in such powders may contain less than 1% of coating agent.

When the medicament to be microencapsulated is of medium or high potency so that a diluent or like excipient is required in fairly high quantities one preferred powder comprises 10% to 95% of optionally microencapsulated excipient and 5% to 90% of microencapsulated medicament wherein the microcapsules have an average diameter of at least $100\mu$ and 90% of which microcapsules have diameters in the range $75\mu$ to $450\mu$.

In such powders the microencapsulated excipient generally comprise 94% to 99.9% of excipient and 0.1% to 6% of coating agent and the microencapsulated medicament generally comprises 94% to 99.9% of medicament and 0.1% to 6% of coating agent.

Normally the excipient is some conventional diluent.

Preferably in such mixed powders, the microcapsules containing the medicament comprise 98% to 99.8% of medicament and 0.2% to 2% of coating agent.

Preferably the coating agent in both sorts of microcapsules, if microencapsulated excipient is used, is the same.

A very wide range of medicaments are suitable for inclusion in the microcapsules of the invention. Such medicaments include antibiotics and other anti-bacterial agents, analgesics, anti-inflammatory agents, anti-hypertensive agents, hypnotics, sedatives, tranquillisers, alkoloids, diuretics and vitamins or most other medicaments frequently used in oral dosage forms.

Suitable antibiotics include penicillins, cephalosporins, tetracyclines, chloramphenicol, streptomycins, and the macrolids. Suitably fully synthetic anti-bacterial agents include nitrofurantoin and the sulphonimides. Suitable anti-inflammatory or analgesic agents include asprin and paracetamol. Suitable psychotropic medicaments include the benzodiazepines. Suitable anti-hypertensive agents include -methyldopa and guanethidine. Suitable diuretics include aminophyline and acetazolamide.

Normally any of the medicaments to be microcapsulated may be used as their conventional salts, hydrates or the like.

Antibacterials and vitamins are particularly suitable medicaments for microencapsulation.

Antibacterials include benzylpenicillin, phenoxymethylpenicillin, ampicillin and its pivaloyloxymethyl or phthalyl esters, amoxycillin, cloxicillin, dicloxicillin, flucloxicillin, carbenicillin, propicillin, methicillin, cephalexin, cephaloridine, cephaloglycine, cephalothin, tetracycline, oxytetracycline, chlorotetracyline, novobiocin, neomycin, chloromphenicol, sulphothiazole, succinyl sulphathiazole, sulphadimidine, streptamycin, erythromycin, fusidic acid, griseofulvin, kanamycin, lincomycin, novobiocin, spiramycin, sulphamethoxy pyrideazine, sulphaphenazole, salicylazosulphapyridine, sulphamethoxazole and trimethoprin.

Suitable vitamins or nutritional suppliments include thiamine, nicotinamide, ascorbic acid, pyridoxine, riboflavine, tryptophan, pantothenates, glycerophospates and mixtures of these and other vitamins.

Other suitable compounds include alcofenac, theophylline, hexobendine, xylamide, 0-(4-methoxyphenylcarbomoyl)-3-diethylaminopropioph-enone oxime.

The powder of the invention may contain one or more medicaments.

The powders of the invention are especially useful when the microencapsulated medicament is one to which humans may become sensitised on repeated contact as the risk of such sensitisation to process operatives is removed or greatly reduced when the medicament is covered with a coating agent.

One class of medicaments to which humans may become sensitized are the β-lactam antibiotics. β-Lactam antibiotics are therefore included among the medicaments which can benefit greatly from presentation as powder of the invention. Such compounds may be in the form of their salts, hydrates, esters or the like.

Thus one aspect of the invention provides a dustless, freeflowing powder comprising 0% to 5% of conventional pharmaceutically acceptable excipients and 95% to 100% of microcapsules which have an average diameter of at least $100\mu$, 90% of which have diameters in the range $75\mu$ to $450\mu$ and which comprise 0.1% to 6% coating agent and 94% to 99.9% β-lactam antibiotic.

Generally, to ensure versatility, such powder contains less than 2% of conventional pharmaceutically acceptable excipients, for example, 0%.

In this aspect of the invention, highly suitable powders consist essentially of microcapsules comprising 97.5% to 99.9% β-lactam antibiotic and 0.1% to 2.5% coating agent which microcapsules have an average diameter between $150\mu$ and $250\mu$, 95% have diameters between $75\mu$ and $450\mu$ and 80% of which have diameters between $100\mu$ and $300\mu$.

Further, in this aspect of the invention, preferred powders consist essentially of microcapsules containing 98% to 99.8% of one of the previously named β-lactam antibiotics and 0.2% to 2.0% of coating agent which microcapsules have an average diameter between $150\mu$ to $250\mu$. The microcapsules in such powders may frequently contain less than 1% of coating agent.

Ampicillin, amoxicillin, the isoxazolylpenicillins, orally active esters of carbenicillin and ampicillin and their conventional salts and hydrates are especially useful β-lactam antibiotics which may be formed into free-flowing powders of the invention.

It is believed that free-flowing, finely divided solids comprising microcapsules containg β-lactam antibiotic coated with from 0.1% to 6% of coating material are novel. It is surprising that microcapsules containing such small quantities of coating material are of good quality and have good tabletting and other processing properties. Therefore, such free-flowing, finely-divided solids are included within the invention.

Generally the most suitable of such free-flowing, finely-divided solids comprise 95% to 100% of microencapsulated β-lactam antibiotic which microcapsules comprise 98% to 99.8% of β-lactam antibiotic and 0.2% to 2% of coating agent.

Particularly preferred such free-flowing, finely-divided solids consist essentially of microcapsules comprising 0.2% to 2% of coating agent and 98% to 99.8% of ampicillin, amoxicillin, an isoxazolylpenicillin, an orally active ester of ampicillin or carbenicillin or conventional salts or hydrates of such penicillins.

Ampicillin trihydrate and amoxicillin trihydrate are especially suitable for inclusion in such free-flowing, finely-divided solids.

Coating agents suitable for use in this invention are pharmaceutically acceptable and include synthetic polymers such as methylcellulose, methylprolylcellulose, polyvinylpyrrolidone, polyvinylacetaldiethylamino acetate, celluloseacetate phthalate, hydroxyethylcellulose, polyvinyl alcohol, sodium carboxymethylcellulose, hydroxypropylmethylcellulose, 2-methyl-5-vinylpyridine methacrylic acid methacrylate copolymer, ethylcellulose and the like and natural gums or resins such as gelatin, acacia, carragheen, alginic acid, tragacanth and certain of their hydrolysis products or the like. The preceeding list is not exhaustive but merely illustrates the range of coating agents which may be used to produce microcapsules.

It is possible to use mixtures of coating agents but this is generally unnecessary.

The powders of this invention may be prepared by spray drying a slurry comprising a suspension of a medicament in a solution of coating agent in a solvent.

Spray drying is a well understood process widely used in industry. However, microencapsulation of a medicament by means of spray drying has not found widespread use on a commercial scale. In those cases where spray drying has been reported as a suitable method of microencapsulation the microcapsules produced have always been relatively small so that the product has been dusty. This may be because only small spray driers have been used. Further, it does not appear to have been discovered that microcapsules may be prepared which contain very small percentages of coating agent and which are also dustless.

Furthermore, the products of the process of this invention have advantages over conventional raw material forms such as:

1. The process produces large dustless, free-flowing powders. The powder is contained within the shell material during processing and the dust produced during mixing and handling operations is markedly reduced or eliminated.
2. Coated products containing thermolabile substances often retain the maximum potency. The conditions of production are mild and the stability characteristics of the product may be optimised.
3. The process control is precise. The residual solvent content can usually be maintained at a required level and the characteristics of the coated materials are generally consistant.
4. The method can be incorporated as a last stage in the manufacturing process of many pharmaceuticals. The centrifuged or filtered wet cake of the product may be reslurried in the polymer solution, homogenised and spray dried to produce the product. The processing costs are frequently no greater than those of conventional methods of manufacture and the plant capacity can be adjusted within a large range to suit the product.
5. The spray dried powders may be designed to be suitable for compounding into tablets, capsules, paediatric syrups and other dosage forms. The use of such coated powders often has a number of advantages over the conventional raw material forms. For example
   a. Comminution stages in pharmaceutical processing are obviated and all operations are relatively dust free which improves the environment, simplifies cleaning operations and often minimises raw material losses.
   b. The pharmaceutical processing costs are often decreased while the plant capacity is frequently increased. For example, the preparation of tablets is often reduced from a multistage operation to a two stage process, the manufacture of capsules is simplified (in the case of low potency drugs, the capsule fill material is generally prepared by a single compaction process; for high potency drugs, the coated powders are frequently filled directly) and the weight variation of products in capsules, syrup and tablet manufacture are often reduced due to the improvements in the flow properties of powders containing the spray dried particles.
6. The quality of products prepared from coated powders is generally improved. For example
   a. Tablets can be prepared which are elegant in appearance, hard and non-friable. The weight of active material per tablet may be made high and the size of tablets per dose may be made small. The tablets often disintegrate rapidly compared with normal products and the biopharmaceutical properties of the dosage form are often optimised.
b. Capsules with improved biopharmaceutical properties can be prepared.
c. The physical appearance of syrup powders may be improved.
d. The chemical stability of pharmaceuticals in dosage forms is often optimised through the precise control of moisture or other solvent levels and/or the protection offered by a coating material which protects the powder in an incompatible environment.

As previously stated, such useful products may be provided by a process containing a spray drying stage.

Accordingly, the present invention provides a process for the preparation of a pharmaceutical formulation which contains or is derived from a powder of this invention which process comprises formng a slurry of medicament in a solution of a coating agent which slurry may contain conventional pharmaceutical excipients which may form up to 95% of the suspended solids, spray drying the slurry and formulating the resulting microcapsules.

If the spray dried material may be required for different types of dosage forms, then in one aspect, the present invention provides a process for the preparation of a pharmaceutical formulation which process comprises forming a slurry of a medicament in a solution of coating agent which slurry contain up to 5% of conventional pharmaceutical excipients as hereinbefore defined, spray drying the slurry and formulating the resulting microcapsules.

Obviously, formulation of the microcapsules may take place shortly after their production by spray drying or alternatively, formulation may occur separately at a later time. Thus one further aspect of the process of the invention comprises the preparation of the powder comprising the microcapsules while another aspect of this invention comprises the processing of the powder into forms suitable for administration to animals including man.

In order to produce a dustless powder, the microcapsules must have an average diameter greater than $100\mu$. This can generally be achieved if the spray of slurry to be dried is composed of droplets substantially all of which have diameters in the range $100\mu$ to $1000\mu$. Preferably, such droplets should have diameters in the range $150\mu$ to $900\mu$. This is a particularly suitable size range of droplets as it often allows the production of microcapsules of an average diameter of about $150\mu$ to $250\mu$ which is a suitable range of average diameter.

In conventional manner, the ratio of the size of the microcapsule produced to the size of the droplet formed is roughly proportional to the percentage of suspensed solids in the slurry.

Thus one aspect of the process of this invention comprises the formation of a slurry of a medicament in a solution of coating agent which slurry may contain up to 5% of conventional pharmaceutical excipients, dispersing the slurry as droplets substantially of all which have diameters of from $100\mu$ to $1000\mu$ into a spray drying cavity and collecting the resulting microcapsules in conventional manner and thereafter, if desired processing the microcapsules into standard dosage forms.

For reasons of economy, the amount of suspended solids is normally kept as high as compatible with the spray drying apparatus. Thus the suspended solids usually comprise 15% to 66% of the slurry. In the present invention about 33% to about 60% often provides a satisfactory range, 40% to 55% is generally a particularly suitable range while frequently the best results may be achieved by using an approximately 45% to 50% suspension.

Thus in one preferred form this aspect of the invention provides a process comprising the formation of a slurry of a medicament in a solution of a coating agent which slurry may contain 33% to 60% of suspended medicament, dispersing the slurry as droplets substantially all of which have diameters of from $150\mu$ to $900\mu$ into a spray drying cavity and collecting the resulting microcapsules in conventional manner.

If required, small amounts of anti-foaming agents such as octanol or de-flocculants such as polyoxyethylene sorbitan monooleate (Tween 20 -Registered Trade Mark) may be added to the slurry.

The spray drying process of this invention is unusual in that the slurry to be spray dried contains only small quantities of dissolved coating agent, for example, if total suspended solids plus total coating agent amount to 100% then the coating agent present will normally be only about 0.1% to 6%.

Thus one aspect of this invention provides a process which comprises forming a slurry of a medicament in a solution of a coating agent which slurry may contain 33% to 60% of suspended solids as hereinbefore described and in which the dissolved coating agent forms 0.1% to 6% of the total weight of suspended solids plus coating agent, spray drying the slurry and collecting the resulting microcapsules in conventional manner.

In such a process, it is preferable that the slurry is substantially free from excipients.

β-Lactam antibiotics are particularly suitable medicaments for use in this process.

It is more suitable that the slurry contains 0.1% to 2% of dissolved coating agent expressed as a percentage of the total weight of suspended solids plus coating agent and generally it is preferred that the slurry contains less than 1% of coating agent if microcapsules containing only small quantities of coating agent are required.

The slurry to be spray dried may be made in any suitable solvent such as water, ethanol, propanol, chloroform, methylene chloride, acetone, methylethylketone, methyl acetate, ethyl acetate, methanol, trichloroethylene, tetrachloroethylene, carbon tetrachloride or like solvents or homogeneous mixtures of such solvents. Obviously, since it is necessary to spray dry a slurry of the medicament, the choice of solvents is limited to those in which the medicament has low solubility and preferably to those in which the medicament is insoluble or substantially insoluble. Normally, the solubility of the medicament is less than 15% and preferably less than 10%, for example, below 5% at the temperatures used.

If it is desired to use a particular coating agent then the choice of solvent is further limited to those which dissolve the desired coating agent. The solvent should be one in which the coating agent is at least 10% soluble at the temperature of forming, storing and spraying the suspension to be spray dried and preferably at least 20% soluble at that temperature. Microcapsules of good quality are generally most easily prepared if the coating agent is at least 30% soluble in the solvent used.

The medicament and any excipient present in the slurry may already be finely divided. However, if this is not the case, it will be necessary to include a wet milling operation to reduce the particle size of the suspension before the slurry is spray dried. Any convenient conventional method may be used for this purpose. Before the slurry is spray dried it is normally beneficial to homoganise it in conventional manner.

The slurries suitable for spray drying are believed to be novel and as such form as aspect of the present invention.

The process of the invention may take place in any conventional large spray drier but the best results are often obtained from the kind of conventional spray drying equipment shown in FIG. 1. Although large spray driers of this kind are not generally used in the pharmaceutical industry they are well known in other industries where large scale drying apparatus is used. For the present invention the spray drier may be operated in a conventional manner wherein the various operating parameters such as inlet and outlet temperatures, pumping pressures, liquid flow rate, gas flow rate, atomiser design and the like affect the nature of the product in conventional manner.

When using an open cycle drying system of the sort shown in FIG. 1, the homogenised slurry 1, is stored in a tank 2 in which it is agitated by the homogenisor 3, until it is pumped by the high pressure pump 4 to the atomiser 5 at the top of the spray drier. The atomiser 5 is generally of the nozzle type although spinning disc atomisers may be used on wide spray driers. The nozzle atomiser 5, sprays droplets into the drying cavity 6 where the droplets dry in and with a co-current air-flow which originates at the outlet 7. This drying air has been heated to the desired temperature in an air heater 8 before being pumped to the outlet 7. After leaving the outlet 7, the heated air descends through the drying cavity 6 into the bussle 9 where it turns upwards and leaves through the vents 10 from where it passes via a cyclone 11 to the exterior 12. As the air descends inside the dryer, the liquid present in the droplets evaporates to leave microcapsules; this process is completed by the time the air and the materials suspended in it reach the bussle 9. As the air turns upward in the bussle, it precipitates most of the microcapsules which fall through the opening 13 at the bottom of the bussle 9 into a screen system 14 which separates the microcapsules in the desired size range from the fines. The desired microcapsules and fines are respectively deposited in the collection vessels 15 and 16. Any microcapsules present in the air leaving via the cyclone 11 are precipitated and separated into microcapsules of the desired size range and fines by a screen system 17. The desired microcapsules and the fines are respectively deposited in the collection vessels 15 and 18.

The fines generally represent 5% to 10% of the spray dried product and may be added to the initial slurry for recycling thereby minimising losses.

If it is desired to use a solvent which is to be recollected after passing through the apparatus, a condensor system may be included in the apparatus at some point after the cyclone 11. In such conventional closed-cycle spray drier, the heated air is normally replaced by heated solvent vapour.

Both open-cycle and closed-cycle spray driers are equilibrated and operated in conventional manner.

Suitable parameters for an open-cycle spray drier are generally (water as solvent):

| Spray dryer height | 6 – 20 meters |
|---|---|

-continued

| Spray Dryer Chamber diameter | 1 – 3 meters |
|---|---|
| Feed rate of suspension | 25 – 200 lt/hr. |
| Atomizer nozzle diameter | 0.5 – 1.5 mm |
| Atomizer nozzle pressure | 5 – 15 kg/cm$^2$ |
| Rate of air flow | 750 – 1200 kg/hr. |
| Inlet temperature | 150 – 250° C |
| Outlet temperature | 50 – 120° C |

Suitable parameters for a closed-cycle spray dryer are generally:

| Spray dryer height | 6 – 20 meters |
|---|---|
| Spray dryer chamber diameter | 1 – 3 meters |
| Feed rate of suspension | 25 – 200 lt/hr. |
| Atomizer nozzle diameter | 0.5 – 1.5 mm |
| Atomizer nozzle pressure | 5 – 15 kg/cm$^2$ |
| Dry gas, orifice plate pressure drop | 70 – 120 mm WG |
| Inlet temperature | 60 – 130° C |
| Outlet temperature | 40 – 30° C |
| Condenser temperature | 0 – 30° C |

Once the desired microcapsules are isolated they may be stored prior to use or they may be used at once to manufacture dosage forms suitable for administration to animals including man. Such dosage forms may contain conventional pharmaceutical carriers.

Thus in a further aspect, this invention provides a formulated medicament which contains a powder or free-flowing, finely divided solid as hereinbefore defined together with a conventional pharmaceutical carrier.

When used herein the term "formulated medicament" means a medicament suitable for human or veterinary administration which medicament is either in unit dosage form or in the form of a granulate, powder or syrup suitable for reconstitution into a suspension or solution suitable for human or veterinary administration or in the form of a gel or cream or the like for topical application.

Suitable unit dosage forms include tablets, capsules and like conventional shaped pharmaceutical preparations and sachets, ampoules and like conventional containers for unit dosage pharmaceutical preparations.

Powders, granulates, syrups and the like may be presented in bottles or similar containers and may contain multiple doses. Such powders, granulates, syrups and the like may normally be made up into solutions or suspensions suitable for oral administration by the addition of water or other convention liquid accompanied by agitation.

The formulated medicament of the invention normally contains a conventional pharmaceutical carrier. The quantity of such carriers will depend on the type of formulation (for example, whether a tablet, capsule or reconstitutable granulate and so on) and the degree of activity of the medicament (for example, if the medicament is required in 0.5 mg. quantities per dose, it is obvious that a higher proportion of carrier is required than in the case where a medicament is required in doses of 200 mgs. or more).

Tablets are widely used as a convenient oral dosage form. Thus in one aspect, the present invention provides a pharmaceutical tablet comprising microencapsulated medicament together with a conventional pharmaceutical carrier when prepared from a powder or finely-divided, free-flowing solid of the invention.

For high potency medicaments the tablets may, for example, contain about 5% of microcapsules. Tablets containing medium potency medicaments may contain, for example, about 10% to 50% of microcapsules. In general, tablets of low potency medicaments contain at least 60% microcapsules.

Tablets of this invention containing low potency medicaments are especially useful as they may be significantly smaller than the corresponding conventional tablets.

Thus in particularly suitable form this aspect of the invention provides a pharmaceutical tablet comprising 60% to 99.9% of microcapsules together with 0.1% to 40% of a conventional pharmaceutical carrier.

The more suitable microcapsules for tablet manufacture generally contain between 0.1% and 2.5% of coating agent, more suitably contain 0.2% to 2% of coating agent and frequently contain less than 1% of coating agents.

Thus in one aspect this invention provides a pharmaceutical tablet comprising 60% to 99.9% of microencapsulated medicament together with 0.1% to 40% of conventional pharmaceutical carriers wherein the microcapsules comprise 0.1% to 2.5% coating agent, and 97.5% to 99.9% of medicament, and which microcapsules preferably comprise 0.2% to 2% of coating agent and 98% to 99.8% of medicament.

When the tablets contain a single low potency medicament in order to minimise size it is frequently advantageous if that tablet comprises 75% to 99.9% of microcapsules and 0.1% to 25% of conventional pharmaceutical carrier and it is often preferable that the tablet comprises 90% to 99.9% of microcapsules and 0.1% to 10% of a conventional pharmaceutical carrier.

If this is expressed in terms of medicament content, it is believed that for low potency medicaments suitably the tablets contain approximately 75% to 99.6% medicament, more suitably, the tablets contain approximately 80% to 99% medicament and preferably the tablets contain approximately 90% to 98% medicament.

Tablets may be prepared by direct compression of the encapsulated medicament because of the excellent flow and binding properties of the microcapsules. However, the addition of from 0.1% to 2% by weight of a lubricant such as magnesium stearate or stearic acid or the like, generally improves the quality of the tablets. Such tablets normally disintegrate sufficiently readily in the stomach but if it is desired to obtain tablets that disintegrate more rapidly 0.1% to 20% by weight of a conventional disintegrating agent such as starch or the like may be added to the mix before tabletting. Small amounts of flavouring, colouring, preserving and like agents may also be added if required.

The $\beta$-lactam antibiotics are generally suitable medicaments forming into a tablet of this invention. It has been found that especially suitable tablets containing one or more $\beta$-lactam antibiotics contain roughly 85% to 98% of antibiotic. Thus in one aspect, this invention provides a pharmaceutical tablet comprising 85% to 99.5% of microcapsules together with 0.5% to 15% of a conventional pharmaceutical carrier, wherein the microcapsules contain 94% to 99.9% of lactam antibiotic.

In a preferred form such a tablet comprises 90% to 98% of microcapsules together with 2% to 10% of conventional pharmaceutical carrier, wherein the microcapsules comprise 99% to 99.9% of lactam antibiotic and 0.2 to 2% of coating agent.

Certain semi-synthetic penicillins have proved to be readily tabletted when the coating agent is in the range of 0.2% to 1.0%.

Thus when the $\beta$-lactam antibiotic is a semi-synthetic penicillin, it is often the case that suitable tablets may be prepared which comprise 90% to 98% of microcapsules together with 2% to 10% of a conventional pharmaceutical carrier, wherein the microcapsules comprise 99% to 99.8% of a semi-synthetic penicillin and 0.2 % to 1.0% of a coating agent.

If desired, the free-flowing powder to be tabletted may comprise two or more medicaments at least one of which has been microencapsulated as hereinbefore described. In this aspect of the invention there are often two medicaments present both of which have been microencapsulated. Thus it is possible to prepare tablets containing, for example, equal amounts of microencapsulated ampicillin trihydrate and microencapsulated cloxacillin.

The tablets of this invention may be made in conventional tabletting presses. Generally, a powder of the invention or a powder of the invention blended with conventional pharmaceutical carriers may be directly compressed or may be first granulated and then compressed.

When the amounts of conventional pharmaceutical carrier is low, for example, less than 15%, the excellent flow properties of the microcapsule generally allow direct compression to be used. However, if large amounts of conventional pharmaceutical carriers are used, for example, 30% of fillers or 20% of disintegrating agents or the like, then it may be more convenient to granulate the mixture before compressing into tablet form.

The equipment and the operation thereof used in these procedures are those conventionally used in tablet formation.

The granulates of the powders of the invention and of the blended powders and conventional pharmaceutical carriers form aspects of this invention.

The process for the preparation of the tablets of the invention also forms an aspect of this invention. Thus in one aspect, this invention provides a process for the preparation of a pharmaceutical tablet as hereinbefore described which comprises the compression of a powder or free-flowing, finely divided solid of the invention which optionally has been blended with a conventional pharmaceutical carrier and/or optionally has been granulated. Powders or granulates for reconstitution into syrups or the like may be prepared in conventional manner using a powder of the invention in place of the conventional raw material form of the medicament. In such cases, the coating agent is normally one readily soluble in water. In these formulations, the microencapsulated medicament usually forms from about 0.5% to 20% of the solids present. If a $\beta$-lactam antibiotic is used, the microcapsules normally form about 1% to 3% of the solids present. These powders or granulates are often presented in sachets or multidose bottles or the like.

One successful dosage form comprises capsules of hard gelatin or some conventionally used equivalent material containing the medicament.

Use of the microencapsulated medicament of this invention in place of conventional raw materials has advantages such as reduction in weight variations of product in the form of capsules due to the greater ease in filling (due to improved flowability of the microcapsules) and better bioavailability.

Thus in one aspect, the present invention provides a formulated medicament in a unit dosage form comprising a capsule of pharmaceutically acceptable material soluble in digestive juices which capsule contains a powder of this invention optionally together with conventional pharmaceutical carriers and which has optionally been granulated.

Preferably, the capsule is of a hard gelatin.

Generally, the capsule contents have not been granulated.

Frequently, for low potency only small quantities of conventional pharmaceutical carriers are blended with the microencapsulated medicament of the invention prior to the filling of the capsules. Normally, such carriers are present in about 0% to 10% of the weight of the powder and more suitably about 2% to 5% of that weight.

In order to fill the capsule, it is generally only necessary to blend the powder of the invention with the desired carrier and fill directly into the capsule. This is a shorter process than conventionally used to fill capsules.

Thus in this aspect, the invention provides a process for the production of a pharmaceutical dosage form which comprises blending 0% to 10% of conventional pharmaceutical carriers with 100% to 90% microcapsules of the invention and filling the mixture into capsules.

Useful capsules of this invention include those containing 100 mg, 125 mg, 250 mg or 500 mg of ampicillin or amoxicillin or equivalent weights of their trihydrates or such quantities of other β-lactam antibiotics.

The creams of the invention include those in bases suitable for bovine intra-mammary use. Such intromammary creams may include cloxacillin or other β-lactam antibiotics and may be formulated in conventional manner.

The powders of the invention may be used in place of the conventional medicament raw materials in supositories.

In the following Examples, unless otherwise stated, a NIRO TOWER SPRAY DRIER was used. The drier is similar to that shown schematically in FIG. 1 and is approximately 12 meters high and 1.75 meters in diameter. Such apparatus is of an industrially used dosage and was made by Niro Atomizer Limited, Copenhagen, 305 Gladsaxevej, DK-2860 Sobeborg, Denmark.

The coating agents A - P of the Examples are as follows:

| Letter | Coating Agent | Trade Name (If Any) | Supplier |
|---|---|---|---|
| A | Hydroxypropylmethyl-cellulose | Methocel HG60 | Dow |
| B | Hydroxypropylmethyl-cellulose | Pharmacoat | Shinetsu |
| C | 2-methyl-5-vinylpyridine-methacrylic acid methocrylate copolymer | | |
| D | Ethylcellulose | | |
| E | Polyvinylacetaldiethyl-aminoacetate | | |
| F | Celluloseacetatephthalate | | |
| G | Methylcellulose | Celacol MM10 | British Celanese |
| H | Methylcellulose | Celacol M20 | " |
| I | Polyvinylpyrolidone | Plesdone K29-32 | G.A.F. |
| J | Polyvinylpyrolidone | Kollidon 25 | B.A.S.F. |
| K | Sodium Carboxymethyl-cellulose | Coulose P8 | British Celanese |
| L | Gelatin | Protein S | Coroda |
| M | Gelatin | Hydrolysed Gelatin | Leinar |
| N | Polyvinylalcohol | Gelvatol 40–20 | Mosanto |
| O | Hydroxypropylcellulose | Klucel | Hercules |
| P | Hydroxypropylcellulose | Celacol He25 | British Cellanese |

EXAMPLE 1

Preparation of Microencapsulated Ampicillin Trihydrate a. Formation of Slurry

Ampicillin trihydrate (27 kg) obtained from a wet cake of the material taken from a standard commercial production batch was added to a solution of sodium carboxymethylcellulose (K), (0.27 kg); i.e. 1% of medicament weight) in dimineralised water (30 kg). The mixture was stirred during addition. This produced a slurry containing about 47.6% solids in suspension. Some foaming occurred during the continuing agitation but was reduced by the addition of a small quantity of octanol. The suspension was sieved through a 0.3 mm vibrating screen to remove clumps of medicament particles which had not disintegrated during stirring. The sieving stage increased the foam present. The suspension was transferred to feed tank where it was kept stirred in order to maintain an even distribution of medicament particles.

b. Tower Operation

The suspension from the feed tank was pumped through a nozzle atomiomizer at about 33 kg/hr. The nozzle orifice diameter was set at 1.0 mm, the spray angle of the nozzle was set at 80° and the nozzle presure at 11 kg/cm$^2$. A concurrent air flow was pumped through the spray drier at 925 kg/hr. and the temperature of the air adjusted to give an inlet temperature of 160° C and an outlet temperature of 81°–87° C.

The encapsulated powder was collected from the bottom of the tower in a discharge hopper and a cyclone separator. In general, 20% to 25% of the products were recovered in the cyclones and 75% to 80% were collected from the chamber. There was no observable powder present in the exhaust gas leaving the stack.

The product was screened in the apparatus prior to collection to remove particles below $75\mu$ (5% to 10%) and the encapsulated powders were stored for evaluation and pharmaceutical processing.

The spray dired powders consisted of particles composed of an outer porous shell of polymer with an inner core of fine antibiotic powder. The core contained small quantities of air and interspersed strands of polymer. The coates appeared to contain blow holes.

EXAMPLES 2 – 5 a. Slurries containing 27 kg of ampicillin trihydrate were made up as described in Example 1 but containing the following constituents:

| Example No. | Coating Agent | Wt. of Coating Agent (kg) | Water (kg) | Solids In Suspension (%) |
| --- | --- | --- | --- | --- |
| 2 | K | 0.27 | 33 | 45 |
| 3 | K | 0.135 | 33 | 45 |
| 4 | K | 0.135 | 33 | 45 |
| 5 | K | 0.135 | 33 | 45 |

Example 4 produced a large amount of foam which was controlled in Example 5 by the use of an octanol/silicone mixtures as anti-foaming agent. Example 6 also produced a large amount of foam but no silicone was used to reduce this.

b. The tower was operated as described in Example 1. When an atomizer with a spray angle of 8° was used, some deposition of antibiotic on the side walls of the drying chamber was observed. This did not occur when a 45 ° angle nozzle o was used.

| Example No. | Nozzle Oriface (mm) | Spray Angle | Nozzle Pressure (kg/cm) | Approx. Throughput (kg/hr) | Inlet Temp. (° C) | Outlet Temp. (° C) | Air Flow (kg/hr) |
| --- | --- | --- | --- | --- | --- | --- | --- |
| 2 | 1.0 | 80° | 11 | 33 | 138 – 160 | 71 – 78 | 925 |
| 3 | 0.9 | 45° | 9 | 29 | 135 – 14 | 68 – 78 | 925 |
| 4 | 0.9 | 45° | 9 | 30 | 160 | 79 – 81 | 925 |
| 5 | 0.9 | 45° | 9 | 30 | 170 | 74 – 77 | 925 |

EXAMPLES 6 – 14 a. In order to reduce the quantity of foam, the medicament suspension was prepared as follows:

The coating agent solution was prepared in one vessel using a Silverson LZR mixer with standard emulser head attachment. The ampicillin trihydrate suspension was prepared in a second vessel using a Silverson mixer and a turbo-stirrer. The coating agent solution was added to the medicament suspension, mixed and then defoamed with a small quantity of octanol. The suspension was then pumped to a feed tank via a 0.3 mm screen. The suspension was kept stirred in the feed tank to ensure an even distribution of particles.

Slurries containing 22 kg of ampicillin trihydrate were made up as described containing the following constituents:

| Example No. | Coating Agent | Wt. of Coating Agent (kg) | Water (kg) | Solids in Suspension (%) |
| --- | --- | --- | --- | --- |
| 6 | K | 0.054 | 33 | 45 |
| 7 | K | 0.081 | 33 | 45 |
| 8 | K | 0.108 | 33 | 45 |
| 9 | I | 0.11 | 27 | 45 |
| 10 | L | 0.11 | 27 | 45 |
| 11 | N | 0.11 | 30 | 42.5 |
| 12 | A | 0.11 | 27 | 45 |
| 13 | P | 0.11 | 27 | 45 |
| 14 | N | 0.11 | 27 | 45 | b. The tower was operated as described in Example 1 using a 45° angle nozzle and the following conditions:

| Example No. | Nozzle Orifice (mm) | Nozzle Pressure (kg/cm²) | Approx Throughput (kg/hr) | Inlet Temp. (° C) | Outlet Temp. (° C) | Air Flow (kg/hr) |
| --- | --- | --- | --- | --- | --- | --- |
| 6 | 0.9 | 9 | 24 | 162 | 78 – 79 | 800 |
| 7 | 0.9 | 12 – 9 | 23 | 143 – 160 | 64 – 72 | 800 |
| 8 | 0.9 | 9 | 21 | 105 – 140 | 61 – 71 | 800 |
| 9 | 0.9 | 9 | 18 | 140 | 68 – 70 | 800 |
| 10 | 1.0 | 9 | 21 | 150 | 72 – 73 | 925 |
| 11 | 1.0 | 9 | 32 | 150 | 71 – 73 | 800 – 925 |
| 12 | 1.0 | 9 | 29 | 150 | 70 | 925 |
| 13 | 1.0 | 9 | 33 | 150 | 68 – 71 | 800 – 900 |
| 14 | 1.0 | 10 | 28 | 190 – 200 | 81 – 83 | 750 |

The microcapsules produced in Examples 9 – 14 appeared to have continuous coats free of blow holes.

Properties of the Products of Examples 1 – 14 i. Moisture Content:

The moisture content of the product could be maintained accurately at any desired level by controlling inlet and outlet temperatures of the spray drier. This may be seen in Table 1. The results quoted are an average of several determinations because the spray drier was not operating under equilibrium conditions as only small samples were used. Under equilibrium conditions and when the fractions from the drying chamber and cyclone are continuously removed, the residual moisture may be controlled to within ± 0.5%.

Table 1: Moisture Content of Products from the Drying Chamber for Examples 1-14

Table 5-continued

| Bulk Densities of Products of Examples 1 – 14 | | | | | | |
|---|---|---|---|---|---|---|
| Example No: | 8 | 9 | 10 | 11 | 12 | 13 | 14 |
| Bulk Density: | 0.54 | 0.48 | 0.48 | 0.54 | 0.49 | 0.46 | 0.50 | vii. Disintegration Time:

It was found that the coating agent shells dissolved on contact with the water to liberate the encapsulated powder as a uniformly dispersed suspension of particles of diameter less than 45μ. It was found that the disintegration rate depended upon the coating agent and its concentration as may be seen in Table 6.

Table 6

| Disintegration Time of some Products of Examples 1 – 14 | | | | | | |
|---|---|---|---|---|---|---|
| Example No: | 1 | 5 | 6 | 7 | 8 | 9 |
| Disintegration Time (mins): | 10 | 7 | 5 | 5 | 7 | 2 |

EXAMPLES 15 – 56

Powders consisting of microcapsules of ampicillin trihydrage (99%) coated with a coating agent (1%) were prepared by a method analogoues to that described in the previous Examples except that the nozzle atomiser was replaced by a spinning disc atomiser. The moisture contents of these powders were determined by the Karl Fischer method. The potency of the product was determined in conventional manner. The $T_{90}$ of the products for Examples 41 – 56 was in all cases at least twice that of the untreated raw material. The results obtained were:

| Example No: | Coating Agent | Inlet Temp. (° C) | Outlet Temp. (° C) | Moisture (%) | Potency (%) |
|---|---|---|---|---|---|
| 15 | K | 180 | 73 | 13.5 | 84 |
| 16 | K | 150 | 64 | 13.1 | 83 |
| 17 | K | 160 | 59 | 13.1 | 83 |
| 18 | K | 158 | 68 | 13.2 | 83 |
| 19 | K | 190 | 71 | 12.5 | 85 |
| 20 | K | 150 | 72 | 12.2 | 82 |
| 21 | K | 125 | 67 | 13.1 | 85 |
| 22 | K | 173 | 70 | 12.5 | 84 |
| 23 | K | 140 | 68 | 12.6 | 84 |
| 24 | K | 170 | 64 | 13.5 | 83 |
| 25 | K | 160 | 70 | 12.8 | 83 |
| 26 | K | 140 | 70 | 13.1 | 84 |
| 27 | K | 140 | 75 | 9.3 | — |
| 28 | K | 140 | 85 | 5.3 | — |
| 29 | K | 140 | 90 | 3.8 | — |
| 30 | K | 140 | 54 | 13.6 | 83 |
| 31 | K | 140 | 60 | 13.8 | 84 |
| 32 | K | 140 | 65 | 13.8 | 82 |
| 33 | K | 140 | 67 | 13.8 | 83 |
| 34 | K | 140 | 70 | 13.5 | 83 |
| 35 | K | 140 | 72 | 13.3 | 85 |
| 36 | K | 140 | 73 | 13.5 | 83 |
| 37 | K | 137 | 775 | 13.2 | 83 |
| 38 | K | 150 | 77 | 12.9 | 83 |
| 39 | K | 170 | 74 | 13.3 | 83 |
| 40 | K | 190 | 75 | 13.2 | 88 |
| 41 | K | 145 | 65 | 13.2 | 82 |
| 42 | P | 145 | 65 | — | 83 |
| 43 | J | 145 | 65 | 13.5 | 83 |
| 44 | O | 145 | 65 | 13.1 | 82 |
| 45 | G | 145 | 65 | 14.5 | 84 |
| 46 | A | 145 | 65 | 13.1 | 82 |
| 47 | M | 145 | 65 | 13.0 | 83 |
| 48 | L | 145 | 65 | 13.5 | 84 |
| 49 | I | 145 | 65 | 12.8 | 85 |
| 50 | G | 145 | 65 | 12.6 | 84 |
| 51 | N | 145 | 65 | 13.4 | 83 |
| 52 | L | 145 | 65 | 12.9 | 84 |
| 53 | A | 145 | 65 | 12.8 | 84 |
| 54 | B | 145 | 65 | 13.6 | 86 |
| 55 | H | 145 | 65 | 13.6 | 85 |
| 56 | M | 145 | 65 | 12.9 | 84 |

The potency of ampicillin trihydrate raw materials in products of Examples 15 – 29 and 41 – 48 was 83%, that of Examples 30 – 40 was 84% and that of Examples 49 – 56 was 86%.

The results of Examples 15 – 56:
i. The moisture contents of the samples are generally controlled predominently by the outlet temperature of the spray drier. The moisture contents of the spray dried products can be controlled precisely and accurately.
ii. The potencies of the ampicillin trihydrate samples within the microencapsulated products are not adversely affected by the spray drying process.
iii. The accelerated shelf-like suitabilities of encapsulated powders, prepared from conventional raw materials are normally greater than those of the untreated raw materials.
iv. The resistance to decomposition at high temperatures of spray dried powders prepared from ampicillin trihydrate wet cake, are greater than those of the untreated raw materials produced by the conventional manufacturing method.
v. The shelf-life shability of ampicillin trihydrate in the spray dried form should be significantly improved.

EXAMPLE 57

In a manner analogous to that described in Example 1, a suspension was prepared consisting of water (40 kg), amoxicillin trihydrate (32.3 kg) and coating agent I (0.242 kg). Octanol (10 ml) was included to reduce foaming. This suspension was pumped to the nozzle atomiser at a rate of 25 kg/hr (the nozzle orifice was set at 0.9 mm and the nozzle angle at 45°) where it was sprayed into the co-current air stream which was flowing at a rate of 850 kg/hr. The inlet air temperature was 160° C and the outlet air temperature was 65° C – 67° C.

The product collected from the spray dryer after the internal separation of fines consisted of amoxicillin trihydrate encapsulated with 0.75% of polyvinyl pyrrolidone. The microcapsules were found to have an average diameter of roughly 170μ.

Similarly, mocrocapsules of amoxicillin trihydrate could be prepared comprising 98.5% amocxicillin trihydrate and 1.5% of a coating agent selected from A to M.

EXAMPLE 58

By using the process of Example 9, dustless, free-flowing powders consisting of microcapsules of ampicillin trihydrate in coating agent I were made with the following compositions:

Table 1

Moisture Content of Products from the Drying Chamber for Examples 1 – 14

Figure 2:
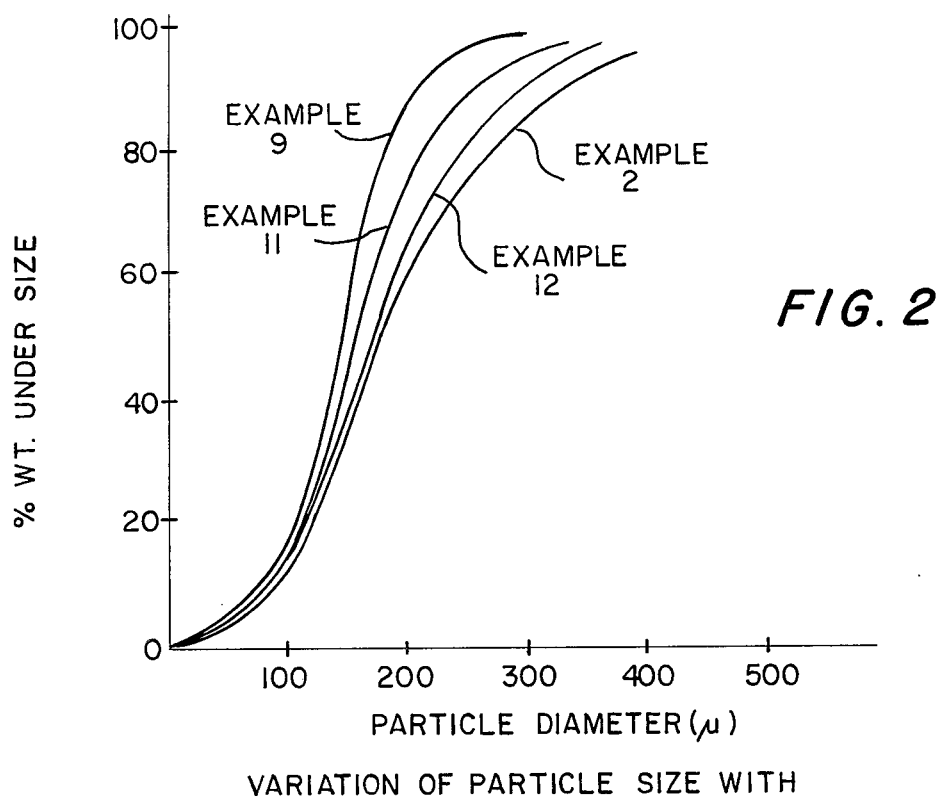
Figure 3:
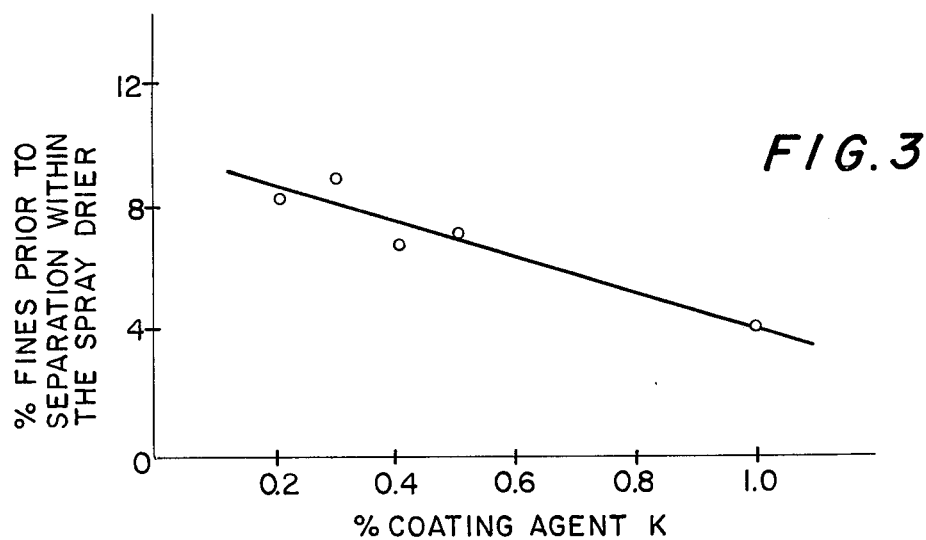

| Example No. | Inlet Temperature °C | Outlet Temperature °C | Moisture % |
|---|---|---|---|
| 1 | 160 | 81 – 74 | ± 0.5 |
| 2 | 138 – 160 | 71 – 74 | 13.9 ± 0.5 |
| 3 | 135 – 142 | 68 – 78 | 16.8 ± 0.5 |
| 4 | 160 | 78 – 81 | 14.7 ± 0.7 |
| 5 | 170 | 74 – 77 | 13.2 ± 0.5 |
| 6 | 162 | 78 – 79 | 13.0 |
| 7 | 143 – 160 | 64 – 72 | 14.0 |
| 8 | 105 – 140 | 61 – 71 | 17.3 |
| 9 | 140 | 68 – 70 | 13.7 |
| 10 | 150 | 72 – 73 | 14.0 ± 0.2 |
| 11 | 150 | 71 – 73 | 14.1 ± 0.1 |
| 12 | 150 | 70 | 14.8 ± 0.4 |
| 13 | 150 | 68 – 71 | 14.2 ± 0.4 |
| 14 | 190 – 200 | 81 – 83 | 12.3 ± 0.5 |
| a - | Reduced from 16.8 | by additional | drying |
| b - | " " 13.8 | " " | " |
| c - | " " 14.1 | " " | " |
| d - | " " 14.5 | " " | " |
| e - | " " 13.8 | " " | " | ii. Potency:

The potency of the raw material and the microencapsulated product were effectively the same.

iii. Stability:

The accelerated stability results obtained indicated that the microencapsulated medicament is likely to have considerably longer shelf life than the untreated raw material. The $T_{90}$ is the time in hours at 80° C required for the material to undergo 10% decomposition. For Examples 8-14 the $T_{90}$ for the microencapsulated material was at least 3 times as long as for the raw material.

iv. Particle Size Distribution:

In general, the particles obtained from the cyclone fraction are smaller than those obtained from the drying chamber fraction and there is usually about four times as much product collected from the chamber fraction as from the cyclone fraction. FIG. 2 shows the size distributions in the powders obtained by mixing cyclone and chamber fractions prior to separation of the fines, It has been shown that - a. the average microcapsule size of each product lies between 150$\mu$ and 200$\mu$.
b. Before separation, 3% to 10% of the product is composed of fines (particles with diameters below 75$\mu$).
c. The proportion of fines is related to the quantity of the coating agent used (see FIG. 3) and the nature of the agent.
d. The proportion of fines is related to the gas flow rate as the greatest amount of fines occurred at the highest flow rates and the smallest quantity of fines were produced at the lowest flow rate.
e. The diameter of the spray dried particles can be increased and the proportion of fines reduced by increasing the concentration of solids in the suspension to be spray dried, increasing the spray angle and orifice diameter of the atomising nozzle, increasing the diameter of the chamber and minimising the gas flow through the drier.

v. Friability:

Samples of the spray dried products taken from the chamber fractions of the Experiments 1 – 14 were sieved to select microcapsules of diameter greater than 125$\mu$ and these microcapsules were then tested for friability in conventional manner by subjecting the microcapsules to stress and determining the quantities of particles produced of diameter less than 125$\mu$. The results in Table 2 were obtained and show that friability is low Table 2 Friability of Microcapsules Produced in Examples 2 and 5 – 14

Table 2

Friability of Microcapsules Produced in Examples 2 and 5 – 14

| Example No: | 2 | 5 | 6 | 7 | 8 | 9 | 10 | 11 | 12 | 13 | 14 |
|---|---|---|---|---|---|---|---|---|---|---|---|
| % Friability: | 0.1 | 0.1 | 0.3 | 0.2 | 0.1 | 0.6 | 0.6 | 0.2 | 1.0 | 1.2 | 1.4 |

The results of this test indicate that the microcapsules are sufficiently non-friable to resist substantial break up during blending, tabletting, handling and the like.

vii. Flow Properties:

The angles of repose (that is the maximum angle formed by a static heap of powder resting on a plane horizontal surface to that surface) of some of the products of Examples 1 – 14 are shown in Table 3. The angle of repose for the ampicillin trihydrate raw material was 64°.

Table 4

Angle of Repose Measurements (Chamber Friction) of Products of Examples 1, 4, 6 – 14

| Example No: | 1 | 4 | 6 | 7 | 8 | 9 | 10 | 11 | 12 | 13 | 14 |
|---|---|---|---|---|---|---|---|---|---|---|---|
| Angle of Repose: | 29° | 32° | 39° | 31° | 39° | 28° | 27° | 38° | 31° | 31° | 38° |

This test indicates that the flow rate characteristics of the powders are improved.

vi. Bulk Densities:

Bulk densities of the microencapsulated material are less than that of the raw material because of the large volumes of air trapped between the particles and the small volumes of air actually within the particles. Table 5 shows that the bulk density of the products is often about 20% to 30% below that of the raw material which in this case is 0.67. Chamber fractions and cyclone fractions are approximately equal.

Table 5

Bulk Densities of Products of Examples 1 – 14

| Example No: | 1 | 2 | 3 | 4 | 5 | 6 | 7 |
|---|---|---|---|---|---|---|---|
| Bulk Density: | 0.51 | 0.52 | 0.52 | 0.48 | 0.47 | 0.49 | 0.52 |

| Medicament % | Coating Agent I % |
| --- | --- |
| 96.0 | 4.0 |
| 97.0 | 3.0 |
| 97.5 | 2.5 |
| 98.0 | 2.0 |
| 98.5 | 1.5 |
| 99.0 | 1.0 |
| 99.2 | 0.8 |
| 99.25 | 0.75 |

EXAMPLE 59

In a manner exactly analogous to that used in Example 9, a suspension was prepared consisting of water (60 kg), coating agent L (0.4 kg), asprin (40 kg) and polyoxyethylene sorbitan monooleate (30 g) (as defloculating agent) was prepared and fed at 25 kg/hr to a nozzle atomizer (nozzle orifice = 0.9 mm, nozzle angle = 45°) through which it was dispersed into a co-current stream of air flowing at 850 kg/hr. The inlet temperature was maintained in the range 170° C – 190° C and the outlet temperature was 80° C – 100° C. After internal screening to remove fines, the dry dustless, free-flowing powder collected consisted of micorcapsules of asprin (99%) coated with a hydrolysed protein (1%). The average diameter of the microcapsules was in the range 170μ to 200μ and the powder contained less tha 1% of microcapsules of diameter less than 75μ.

An equivalent powder of paracetamol was produced by replacing the asprin with paracetamol.

Microcapsules of asprin coated with agent L could readily be prepared containing as little as 0.5% coating agent but those containing approximately 1% coating agent were preferred.

EXAMPLE 60

In a manner analogous to that of Example 62, 30 kg of slurry was prepared containing potassium phenethicillin (25%), coating agent I (0.25%) and chloroform (74.75%). This slurry was pumped at a rate of 30 kg/hr through an atomizer nozzle having an orifice diameter of 0.9 mm and a nozzle angle of 45°. The inlet temperature was 100° C – 120° C and the outlet temperature was 60° C – 70° C. After internal screening, the product was a dustless, free-flowing powder of microcapsules comprising potassium phenethicillin (99%) microencapsulated with polyvinylpyrrolidone (1%).

EXAMPLE 61

The following β-lactam antibiotics were microencapsulated by a process analogous to that of Example 13:
  Cloxacillin sodium
  Flucloxacillin sodium
  Cephalexin
  Cephalonidin
  Calcium phenoxymethylpenicillin
  Ampicillin phthalide ester
  Calcium flucloxacillin
  Magnesium flucloxacillin

EXAMPLES 62 – 77

Examples 60 – 77 were carried out in a spray dryer similar to that used for Examples 15 – 56 but fitted with a solvent recovery system. The dryer was pre-equilibrated with solvent vapour in conventional manner. A slurry of suspended medicament (33⅓%), dissolved coating coating agent (x%) and chloroform (to 100%) was prepared by adding milled medicament to the solution of coating agent and homogenising. The suspension was pumped to the top of the spray drying tower and dispersed into a co-current stream of hot solvent vapour at about 120° C. The outlet temperature was approximately 60° C. Dustless, free-flowing powders were produced:

| Medicament | Coating Agent | % Coating Agent In Microcapsules (= 3 × %) |
| --- | --- | --- |
| Potassium phenethicillin | C | 5 |
| Potassium phenethicillin | D | 5 |
| Potassium phenethicillin | C | 2 |
| Potassium phenethicillin | D | 2 |
| Sodium cloxacillin | J | 5 |
| Nicotinamide | A | 5 |
| Nicotinamide | A | 2 |
| Thiaminethydrochloride | G | 5 |
| Aminophylline | F | 5 |
| Aminophylline | F | 2 |
| Alcofennac | D | 5 |
| Alcofennac | E | 2 |
| Hexobenidine | A | 5 |
| Xylamide | A | 5 |
| α-Methyldopa | I | 1 |
| α-Methyldopa | D | 0.75 |

EXAMPLE 78

30 kgs of a suspension comprising ampicillin trihydrate (46%), coating agent B (0.46%), starch (2.3%) and chloroform (to 100%) was prepared as described in Example 1. This suspension was spray dried under the conditions of Example 60 to yield a dustless, free-flowing powder comprising approximately 95% of microencapsulated ampicillin trihydrate and 5% of microencapsulated starch.

EXAMPLE 79

60 kgs of a suspension comprising chloradiazepoxide (8%) and starch (32%) dispersed in a solution of coating agent (0.04) in chloroform (to 100%) was spray dried as described in Example 4. The product of this process was powder comprising 80% of microencapsulated starch and 20% of microencapsulated medicament.

EXAMPLE 80

A mixture of a powder of microencapsulated asprin (94.5%), magnesium stearate (0.5%) and starch (5%) was thoroughly blended. The blended material was tabletted in conventional tabletting presses by a single punch process to produce 250 mg, 500 mg and 800 mg tablets. The tablets produced were of good quality. The 250 mg tablets disintegrated in 30 seconds in water. The microencapsulated asprin used was prepared as described in Example 59 and comprised asprin (99%) and hydrolysed protein (1%).

Similar tablets were prepared using 1% magnesium stearate and 1%, 2%, 4% and 10% starch. The starch used was available as "Primojel".

EXAMPLE 81

Using conventional single punch tabletting techniques tablets of the following formulations:

|                        | A% | B% | C% |
|------------------------|----|----|----|
| Paracetamol microcapsules | 93 | 95 | 98 |
| Starch (STA - RX 1500) | 6  | 4  | 0  |
| Magnesium stearate     | 1  | 1  | 2  |

250 mg Tablets A were of good quality and dissolved in water in 40 seconds. Tablets C dissolved more slowly. The paracetamol microcapsules consisted of medicament (99%) and hydrolysed protein (1%), coating agent L).

EXAMPLES 82 – 84

Using the procedure of Example 6, the following suspensions were prepared in which the medicament was amoxicillin trihydrate and the coating agent was agent K:

| Ex. No: | Wt. of Coating Agent (kg) | Wt. of Medicament (kg) | Water | Octanol (mls) |
|---------|---------------------------|------------------------|-------|---------------|
| 82      | 0.225                     | 45                     | 55kg  | 0             |
| 83      | 0.202                     | 40.05                  | 50lt  | 10            |
| 84      | 0.33                      | 33                     | 41lt  | 10            |

The suspensions were sprayed through a nozzle which had an orifice diameter of 1 mm and a spray angle of 45° at an air flow rate of 115° kg/hr under the following conditions:

| Example No: | Inlet Temp (° C) | Outlet Temp (° C) | Run Time     | Moisture %   |
|-------------|------------------|-------------------|--------------|--------------|
| 82          | 160–162          | 71–76             | 1 hr 32 mins | 12.2 ± 0.5   |
| 83          | 155–162          | 65–70             | 1 hr 20 mins | 12.2 ± 0.5   |
| 84          | 160              | 62–64             | 1 hr 7 mins  | 13.1 ± 0.7   |

Microcapsules were collected from the chamber fraction only due to excessive fragmentation of cyclone fraction microcapsules. Reduction of the air flow rate to 800 kg/hr (with reduction in nozzle diameter to 0.9 mm) allowed intact microcapsules to be collected from the cyclone fraction.

EXAMPLE 85

A mixture of a powder of microencapsuled amoxicillin trihydrate (90%) (as produced in Example 57, 99.25% amoxicillin trihydrate, 0.75% polyvinylpyrrolidone), starch (8%) and magnesium stearate (2%) was tabletted in a conventional tablet press to produce 250 mg of tablets of good quality. These tablets disintegrated in 1.5 minutes in water to release a fine dispersion of amoxicillin trihydrate particles.

EXAMPLE 86

Tablets similar to those of Example 82 were prepared in which the 0.75% polyvinylpyrrolidone was replaced by 1.5% of polyvinylalcohol, hydroxymethylcellulose, methylcellulose or hydrolysed gelatin.

EXAMPLE 87

A single punch press was used to prepare tablets of the following composition from unpre-compressed mixtures of the ingredients:

| Microcapsules       | 79%  |
|---------------------|------|
| Avicel              | 15%  |
| Aerosil             | 0.5% |
| Magnesium stearate  | 1.5% |
| Primojel            | 4%   | where Avicel (Registered Trade Mark) is a microcrystaline cellulose, Aerosil (Registered Trade Mark) is a silica, Priomjel (Registered Trade Mark) is starch; and the microcapsules were respectively a. Sodium cloxacillin (99%) microencapsulated with coating agent I (1%) as prepared by Example 61.
b. Sodium flucloxacillin (99%) microcencapsulated with coating agent I (1%) as prepared by Example 61.
c. A 2.1 mixture of microencapsulated calcium flucloxacillin and microencapsulated amoxicillin trihydrate wherein the sodium flucloxacillin (98%) is coated by coating agent L (2%) and the amoxicillin trihydrate (99%) is coated by coating agent L (1%).

EXAMPLE 88

250 mg Tablets of ampicillin trihydrate were prepared by a single punch process in conventional apparatus. These tablets had the formulation:

| Ampicillin trihydrate | 94%  } Microcapsules |
| Coating Agent         | 0.5% |
| Magnesium stearate    | 0.5% |
| Starch (Primojel)     | 5%   |

The coating agent was variously I, J, L, N, K, A and P.

EXAMPLE 89

Spray dried microencapsulated product from Example 6 was loaded in a blender and mixed with 0.5% magnesium stearate for eight minutes. The mixture was transferred to a Zarasi capsule filling machine and filled into No. 2 capsules (250 mg. dose).

Similarly, the products of Examples 7 to 14 and 42 to 78 were filled into No. 2 or No. 0 (500 mg) capsules.

Capsules could be filled without pre-blending with magnesium stearate but the presence of the lubricant was advantageous.

EXAMPLE 90

Spray dried microencapsulated product from Example 10 was loaded into a blender with 0.5% of magnesium stearate and the mixture blended for eight minutes. The mixture was fed into a roller compactor by means of a transit tube and roller compacted to produce a compact. This compressed flake was passed through a 14 mesh sieve (U.K. size) to form granules. The granules thus formed were filled into capsules in standard equipment to produce capsules containing the equivalent of 125 mg, 250 mg or 500 mg ampicillin.

Using this procedure, 250 mg capsules were filled with the product of Examples 7 to 14 and 48 to 79.

What we claim is:

1. A powder comprising 0% to 95% of conventional pharmaceutical excipients and 5% to 100% of microcapsules, having an average diameter of from 100 $\mu$ to 300 $\mu$ and which consist of 94% to 99.9% of a $\beta$-lactam antibiotic coated by 0.1% to 6% of polyvinylpyrrolidone.

2. A powder according to claim 1 comprising 0% to 5% of conventional pharmaceutical excipients.

3. A powder according to claim 1 comprising 0% to 2% of conventional pharmaceutical excipients.

4. A powder according to claim 1 comprising 1% to 1% of conventional pharmaceutical excipients.

5. A powder according to claim 1 which contains 98% to 99.8% of ampicillin trihydrate or amoxycillin trihydrate as the β-lactam antibiotic coated by 0.2% to 2% of polyvinylpyrrolidone.

6. A powder according to claim 1 wherein the microcapsules comprise 98.0% to 99.8% of β-lactam antibiotic and 0.2% to 2.0% of polyvinylpyrrolidone.

7. A powder according to claim 6 wherein the microcapsules comprise 98.0% to 99.8% of β-lactam antibiotic and 0.2% to 2.0% of polyvinylpyrrolidone.

8. A powder according to claim 6 wherein the microcapsules comprise 99.0% to 99.8% of β-lactam antibiotic and 0.2% to 1.0% of polyvinylpyrrolidone.

9. A powder according to claim 8 wherein at least 90.0% of the microcapsules have diameters in the range of 75μ to 450μ.

10. A powder according to claim 6 wherein at least 95% of the microcapsules have diameters in the range of 75μ to 450μ.

11. A powder according to claim 6 wherein at least 99% of the microcapsules have diameters in the range of 75μ to 450μ.

12. A powder according to claim 11 wherein at least 80% of the microcapsules have diameters in the range of 100μ to 300μ.

13. A powder according to claim 12 wherein the average microcapsule diameter is from 150μ to 250μ.

14. A powder according to claim 13 wherein the average microcapsule diameter is from 175μ to 225μ.

15. A powder according to claim 4 comprising 98% to 100% of microcapsules, which microcapsules have an average diamter of at least 100μ, 90% of which microcapsules have diameter in the range of 75μ to 450μ, and which microcapsules consist of 0.1% to 2.5% polyvinylpyrrolidone and 97.5% to 99.9% of β-lactam antibiotic.

16. A powder according to claim 1 which microcapsules have an average diameter between 150μ to 250μ, 95% have diameters between 75μ to 450μ and 80% have diameters between 100μ to 300μ and which microcapsules consist of 98% to 99.9% β-lactam antibiotic and 0.2% to 2% polyvinylpyrrolidone.

17. A powder according to claim 16 in which the amount of polyvinylpyrrolidone is 0.2% to 1.0%.

18. A powder according to claim 1 comprising 10% to 95% of microencapsulated excipient and 5% to 90% of microencapsulated β-lactam antibiotic wherein the microcapsules have an average diameter of at least 100μ and 90% of which microcapsules have diameters in the range of 75μ to 450μ.

19. A powder according to claim 18 wherein the microcapsules containing the β-lactam antibiotic consist of 98% to 99.9% of β-lactam antibiotic and 0.2% to 2.00% of polyvinylpyrrolidone.

20. A powder according to claim 1 comprising 0% to 5% of conventional pharmaceutical excipients and 95% to 100% of microcapsules which have an average diameter of at least 100μ, 90% of which have diameters in the range of 75μ to 450μ.

21. A powder according to claim 20 consisting of microcapsules containing 98% to 99.8% of β-lactam antibiotic and 0.2% to 2.0% of polyvinylpyrrolidone, which microcapsules have an average diameter of from 150μ to 300μ.

22. A powder according to claim 20 wherein the β-lactam antibiotic is ampicillin, amoxycillin, isoxazolylpenicillin, an orally active ester of ampicillin or carbenicillin or a pharmaceutically-acceptable salt or hydrate of ampicillin, amoxycillin or isoxazolylpenicillin.

23. A powder according to claim 1 wherein the β-lactam antibiotic is ampicillin.

24. A powder according to claim 1 wherein the β-lactam antibiotic is ampicillin, amoxycillin, isoxyzolylpenicillin, an orally active ester of ampicillin or carbenicillin or a pharmaceutically-acceptable salt or hydrate of ampicillin, amoxycillin or isoxazolylpenicillin in the amount of 98% to 99.8% and wherein the amount of polyvinylpyrrolidone is 0.2% to 2.0%.

25. A powder according to claim 1 wherein the β-lactam antibiotic is ampicillin trihydrate.

26. Microcapsules according to claim 1 wherein the β-lactam antibiotic is amoxycillin trihydrate.

27. A powder which have an average diameter of from 100μ to 300μ and which consist of 94% to 99.9% of a β-lactam antibiotic coated by 0.1% to 6% of polyvinylpyrrolidone.

28. A free-flowing, finely-divided solid which consists of microcapsules which have an average diameter of from 150μ to 300μ and which consist of 98% to 99.8% of ampicillin trihydrate or amoxycillin trihydrate coated by 0.2% to 2% of polyvinylpyrrolidone.

29. Microcapsules according to claim 27 wherein the amount of polyvinylpyrrolidone is 0.2% to 2.0%.

30. Microcapsules according to claim 27 wherein the amount of polyvinylpyrrolidone is 0.2% to 1.0%.

31. Microcapsules according to claim 27 in the form of a free-flowing, finely-divided solid.

32. Microcapsules according to claim 31 wherein the β-lactam antibiotic is ampicillin, amoxycillin, isoxazolylpenicillin, an orally active ester of ampicillin or carbenicillin or a pharmaceutically-acceptable salt or hydrate of ampicillin, amoxycillin or isoxazolylpenicillin in the amount of 98% to 99.8% and wherein the amount of polyvinylpyrrolidone is 0.2% to 2.0%.

33. Microcapsules according to claim 31 wherein the β-lactam antibiotic is ampicillin trihydrate.

34. Microcapsules according to claim 31 wherein the β-lactam antibiotic is amoxycillin trihydrate.

35. Microcapsules according to claim 27 which comprise 97.5% to 99.9% of β-lactam antibiotic and 0.1% to 2.5% of polyvinylpyrrolidone.

36. Microcapsules according to claim 35 which comprise 98.0% to 99.8% of β-lactam antibiotic and 0.2% to 2.0% of polyvinylpyrrolidone.

37. Microcapsules according to claim 27 which comprise 99.0% to 99.8% of β-lactam antibiotic and 0.2% to 1.0% of polyvinylpyrrolidone.

38. Microcapsules according to claim 37 wherein at least 90.0% of the microcapsules have diameters in the range of 75μ to 450μ.

39. Microcapsules according to claim 27 wherein at least 95% of the microcapsules have diameters in the range of 75μ to 450μ.

40. Microcapsules according to claim 27 wherein at least 99% of the microcapsules have diameters in the range of 75μ to 450μ.

41. Microcapsules according to claim 27 wherein at least 80% of the microcapsules have diameters in the range of 100μ to 300μ.

42. Microcapsules according to claim 27 wherein the average microcapsule diameter is from 150μ to 250μ.

43. Microcapsules according to claim 27 wherein the average microcapsule diameter is from 175μ to 225μ.

44. Microcapsules according to claim 27 which microcapsules have an average diameter of at least 100μ, 90% of which microcapsules have diameters in the range of 75μ to 450μ, and which microcapsules consist of 97.5% to 99.9% of β-lactam antibiotic and 0.1% to 2.5% polyvinylpyrrolidone.

45. Microcapsules according to claim 27 which microcapsules have an average diameter between 150μ to 250μ, 95% have diameters between 75μ and 450μ and 80% have diameters between 100μ to 300μ and which microcapsules consist of 98% to 99.9% β-lactam antibiotic and 0.2% to 2% polyvinylpyrrolidone.

46. Microcapsules according to claim 45 in which the amount of polyvinylpyrrolidone is 0.2% to 1.0%.

47. Microcapsules according to claim 27 which microcapsules have an average diameter of at least 100μ and 90% of which microcapsules have diameters in the range of 75μ to 450μ.

48. Microcapsules according to claim 27 wherein the β-lactam antibiotic is ampicillin, amoxycillin, isoxazolylpenicillin, an orally active ester of ampicillin or carbenicillin or a pharmaceutically-acceptable salt or hydrate of ampicillin, amoxycillin or isoxazolylpenicillin.

* * * * *